(12) United States Patent
Fitzgerald et al.

(10) Patent No.: US 9,737,913 B2
(45) Date of Patent: Aug. 22, 2017

(54) POUCH CLEANING ASSEMBLY FOR AN ASEPTIC FILLER

(71) Applicant: Scholle Corporation, Northlake, IL (US)

(72) Inventors: Sean Fitzgerald, West Dundee, IL (US); Jeroen Pieter Fiere, 's-Gravendeel (NL); David Bellmore, DeWitt, MI (US)

(73) Assignee: Scholle IPN Corporation, Northlake, IL (US)

( * ) Notice: Subject to any disclaimer, the term of this patent is extended or adjusted under 35 U.S.C. 154(b) by 0 days.

(21) Appl. No.: 14/860,695

(22) Filed: Sep. 21, 2015

(65) Prior Publication Data
US 2017/0081065 A1    Mar. 23, 2017

(51) Int. Cl.
| | |
|---|---|
| *B65B 55/24* | (2006.01) |
| *A61L 2/00* | (2006.01) |
| *B08B 3/04* | (2006.01) |
| *B08B 3/02* | (2006.01) |
| *B65B 55/02* | (2006.01) |

(52) U.S. Cl.
CPC ............... *B08B 3/041* (2013.01); *A61L 2/00* (2013.01); *B08B 3/022* (2013.01); *B65B 55/022* (2013.01); *B65B 55/027* (2013.01); *B65B 55/24* (2013.01)

(58) Field of Classification Search
None
See application file for complete search history.

(56) References Cited

U.S. PATENT DOCUMENTS

| | | | | |
|---|---|---|---|---|
| 3,183,799 | A * | 5/1965 | Schmidt ................. | B65B 55/10 493/194 |
| 3,336,722 | A * | 8/1967 | Van Der Winden .... | B65B 55/00 422/303 |
| 6,066,081 | A * | 5/2000 | Bachner .................... | B31B 1/80 493/102 |

(Continued)

FOREIGN PATENT DOCUMENTS

| | | |
|---|---|---|
| CN | 104646369 A | 5/2015 |
| EP | 694477 A1 | 1/1996 |

(Continued)

*Primary Examiner* — Michael Barr
*Assistant Examiner* — Cristi Tate-Sims
(74) *Attorney, Agent, or Firm* — The Watson I.P. Group, PLC; Jovan N. Jovanovic; Vladan M. Vasiljevic

(57) ABSTRACT

A pouch cleaning assembly that includes a treatment chamber and a guide assembly. The treatment chamber includes an elongated central channel extending therethrough. The guide assembly having a first side guide bar and a second side guide bar. The guide bars defining a channel therebetween that is structurally configured to facilitate the retention of spouts of a plurality of pouches in slidable engagement along the first and second guide bar. Any abutment of adjacent portions of the plurality of pouches within the treatment chamber define relative points of contact. The channel is positioned within the elongated central channel, wherein the channel is undulating in at least one of a vertical and a horizontal direction along the length thereof sufficient so as to substantially expose the relative points of contact between adjacent ones of the plurality of spouts so as to expose the same to the cleaning preparation.

18 Claims, 16 Drawing Sheets

(56) References Cited

U.S. PATENT DOCUMENTS

| | | | | |
|---|---|---|---|---|
| 8,720,163 B2* | 5/2014 | Melrose | ............... | B65B 7/2835 53/127 |
| 2010/0077701 A1* | 4/2010 | Ehmer | ................. | B65B 55/027 53/425 |
| 2010/0205907 A1 | 8/2010 | Herold et al. | | |
| 2017/0001743 A1 | 1/2017 | Tamarindo | | |

FOREIGN PATENT DOCUMENTS

| | | |
|---|---|---|
| JP | 2016-8055 A | 1/2016 |
| RU | 2529723 C2 | 9/2014 |

* cited by examiner

POUCH CLEANING ASSEMBLY FOR AN ASEPTIC FILLER

CROSS-REFERENCE TO RELATED APPLICATION

N/A

BACKGROUND OF THE DISCLOSURE

1. Field of the Disclosure

The disclosure relates in general to aseptic filling, and more particularly, to a pouch cleaning assembly for an aseptic filler.

2. Background Art

The filling of flexible packaging and pouches is known in the art. Generally, such filling occurs in an environment wherein the package is handled, opened, filled and then recapped. As requirements have become more stringent, the prospect of aseptic filling of flowable material, namely foodstuffs, has become significantly more important.

Aseptic filling is the filling of a product, for example, a foodstuff, in a sterile container. With the product being sterile as well, the foodstuff can keep for extended periods of time without the use of preservatives. Typically, such products are contained in flexible bags (as part of bag in box packaging) or in rigid packaging containers such as blown polymer bottles, or cartons made from paperboard laminations.

Problematically, it has been difficult to utilize standup pouches with fitments in the aseptic filling process. In particular, such standup pouches tend to be difficult to sterilize and it has been costly to apply threaded closures to such packaging. Additionally, it has been a challenge to retain such pouches within cleaning equipment to achieve adequate cleaning of outside surfaces prior to insertion into an aseptic filler or the like. Indeed, a cost effective solution for aseptic filling of standup pouches having fitments has been a challenge.

SUMMARY OF THE DISCLOSURE

The disclosure is directed to a pouch cleaning assembly comprising a treatment chamber and a guide assembly. The treatment chamber includes an elongated central channel extending therethrough. The guide assembly includes a first side guide bar and a second side guide bar. The guide bars defining a channel therebetween that is structurally configured to facilitate the retention of spouts of a plurality of pouches in slidable engagement along the first and second guide bar, wherein any abutment of adjacent portions of the plurality of pouches within the treatment chamber define relative points of contact. The channel is positioned within the elongated central channel. The channel is undulating in at least one of a vertical and a horizontal direction along the length thereof sufficient so as to substantially expose the relative points of contact between adjacent ones of the plurality of spouts so as to expose the same to the cleaning preparation.

In some configurations, the channel is undulating in a back and forth manner, with the channel being substantially planar. In another such configuration, the channel is defined by a plurality of linear segments that are obliquely positioned relative to each other, with the linear segments being substantially planar.

In some configurations, wherein the channel includes a substantially uniform width between a first end and a second end thereof.

In some configurations, the channel is undulating in an up and down manner.

In some configurations, the pouch cleaning assembly further includes a first elongated groove extending along a first side of the channel, and a second elongated groove extending along a second side of the channel. The first and second elongated grooves positioned so that a portion of a spout overlies the first and second elongated grooves as a spout travels along the channel. With such a configuration, cleaning fluid can be directed at a underside surface of a spout that would otherwise be generally inaccessible, but positioned within the aseptic zone.

In some configurations, the treatment chamber further comprises a base and a surround. The base has the central channel defined therein and an upper surface. The surround includes an upper wall and opposing depending sidewalls. The upper wall is spaced apart from the upper surface, with the opposing depending sidewalls extending between the upper wall and the upper surface of the base. The base and the surround defining a cavity with the cavity having a first end and a second end.

In some configurations, the surround further includes at least one opening configured to direct a cleaning preparation into the cavity defined by the base and the surround.

In some configurations, the at least one opening comprises a plurality of openings. Preferably, the plurality of openings are defined in the upper wall.

In some configurations, the first end and the second end of the surround further include a wall extending between the surround and the base. The surround has a substantially uniform cross-sectional configuration.

In some configurations, a manifold is positioned between the surround and the central channel, to, in turn, define a manifold cavity between the manifold and the surround. The manifold has a plurality of openings providing fluid communication between the manifold cavity and the central channel.

In some configurations, the manifold further includes a top wall with a first sidewall and a second sidewall depending from the top wall on opposing sides of the central channel. The sidewalls extending to the upper surface of the base. The plurality of openings are positioned in each of the first sidewall and the second sidewall.

In some configurations, the manifold includes a first end that is spaced apart from the first end of the central channel, and a second end that substantially corresponds to the second end of the central channel.

In some configurations, the manifold further includes a front wall sealingly coupling the first end of the manifold and the surround.

In some configurations, the treatment chamber is in positive flow.

In some configurations, the opening of the surround is positioned proximate the second end of the central channel. An outlet from the treatment chamber being positioned proximate the first end of the central channel, so that the positive flow is directed primarily from the second end toward the first end.

In some configurations, the treatment chamber is in positive flow, with an outlet from the treatment chamber being positioned proximate the first end of the central channel, so that the positive flow is directed primarily toward the first end of the central channel.

In some configurations, a housing is positioned below the treatment chamber. The housing is structurally configured to retain a portion of the pouch outside of the treatment chamber while a portion of the pouch extends through the central channel and into the treatment chamber.

BRIEF DESCRIPTION OF THE DRAWINGS

The disclosure will now be described with reference to the drawings wherein.

DETAILED DESCRIPTION OF THE DISCLOSURE

Figure 1:
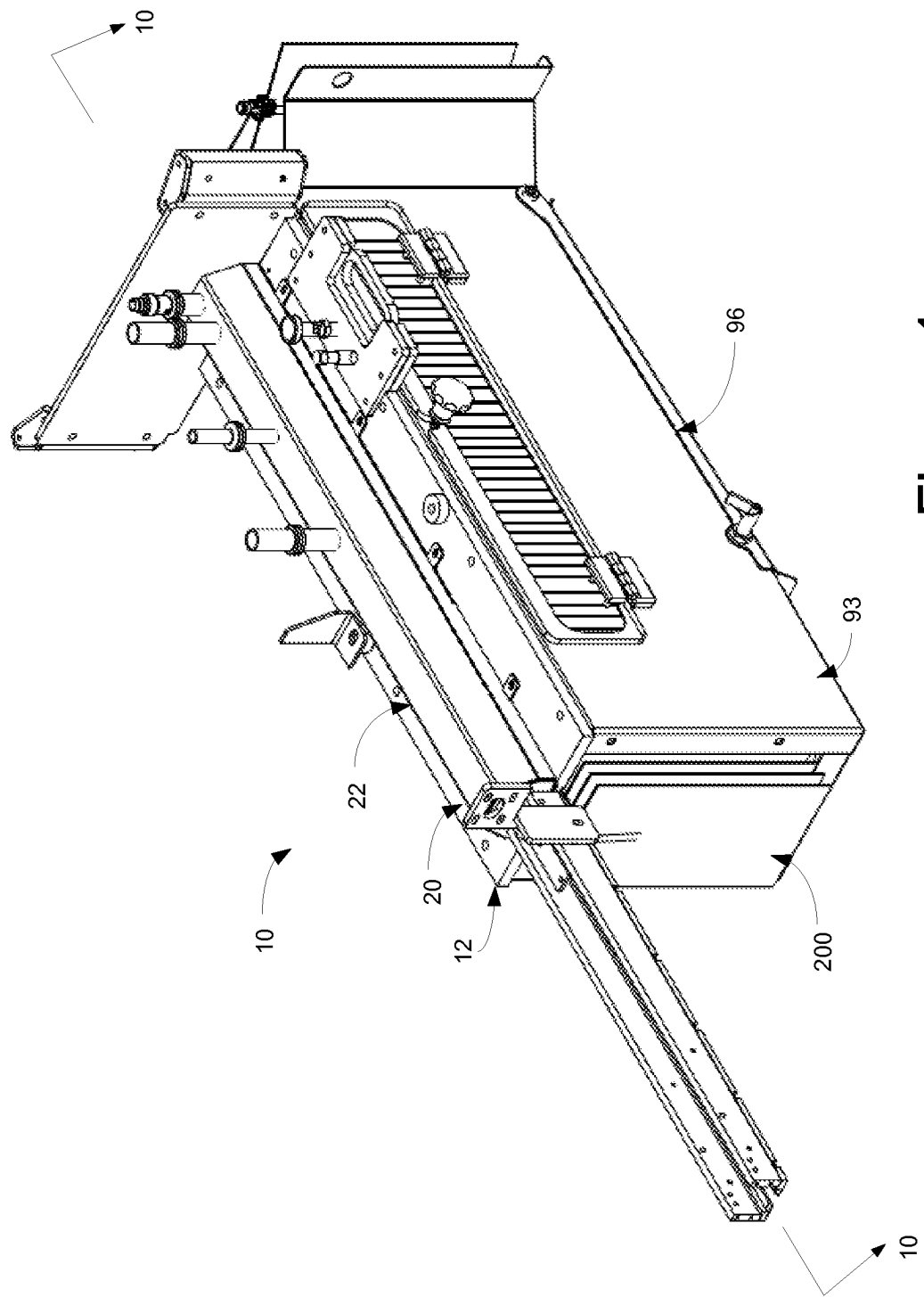
FIG. 1 of the drawings is a top perspective view of the pouch cleaning assembly of the present disclosure, as configured for use in association with a filler, such as an aseptic filler.

While this invention is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Figure 2:
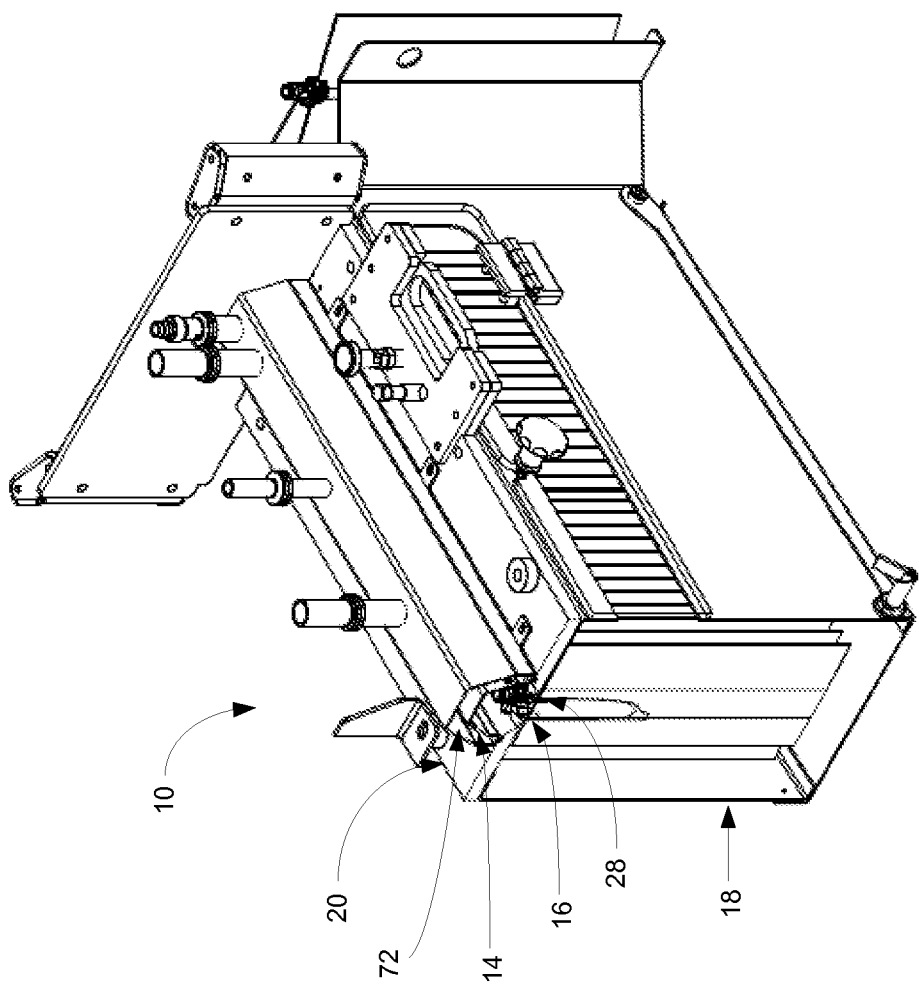
FIG. 2 of the drawings is a cross-sectional perspective view of the pouch cleaning assembly of the present disclosure, showing, in particular, the manifold, and taken generally about lines 2-2 of FIG. 7.
Figure 3:
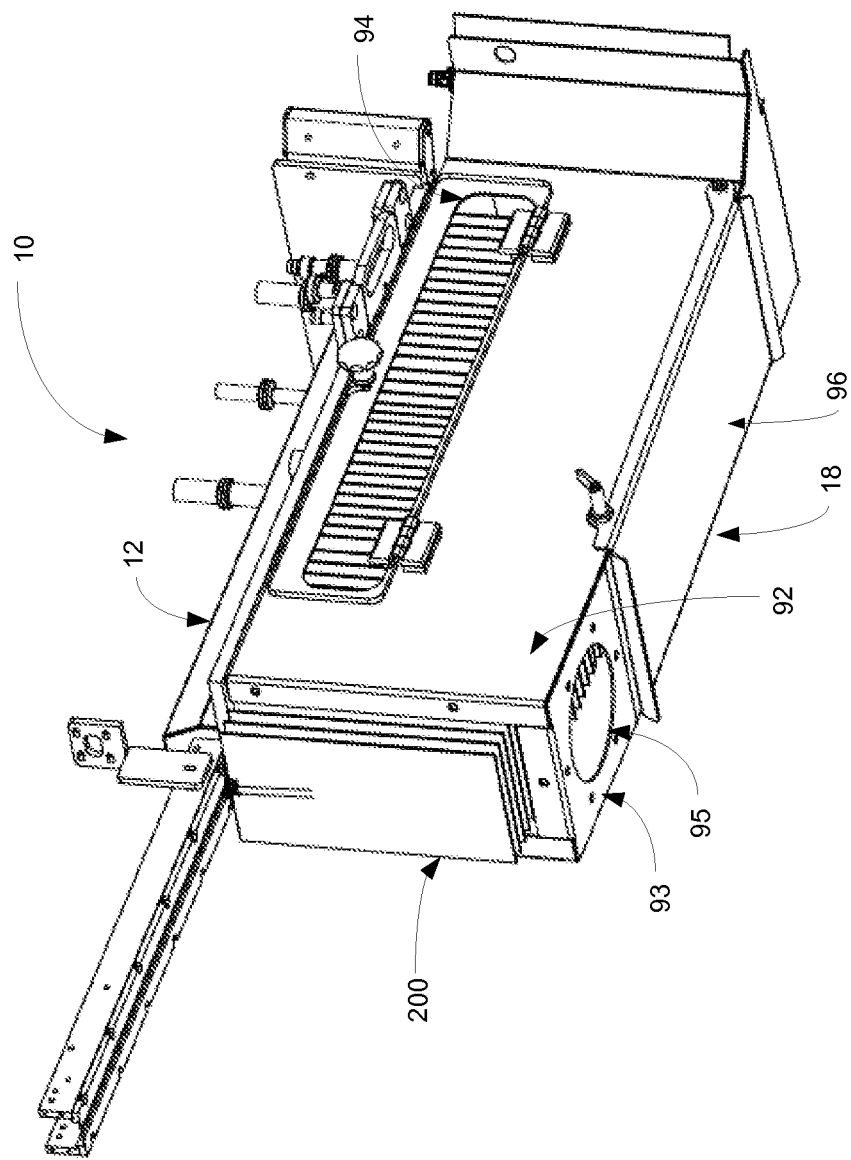
FIG. 3 of the drawings is a bottom perspective view of the pouch cleaning assembly of the present disclosure, as configured for use in association with a filler, such as an aseptic filler.
Figure 4:
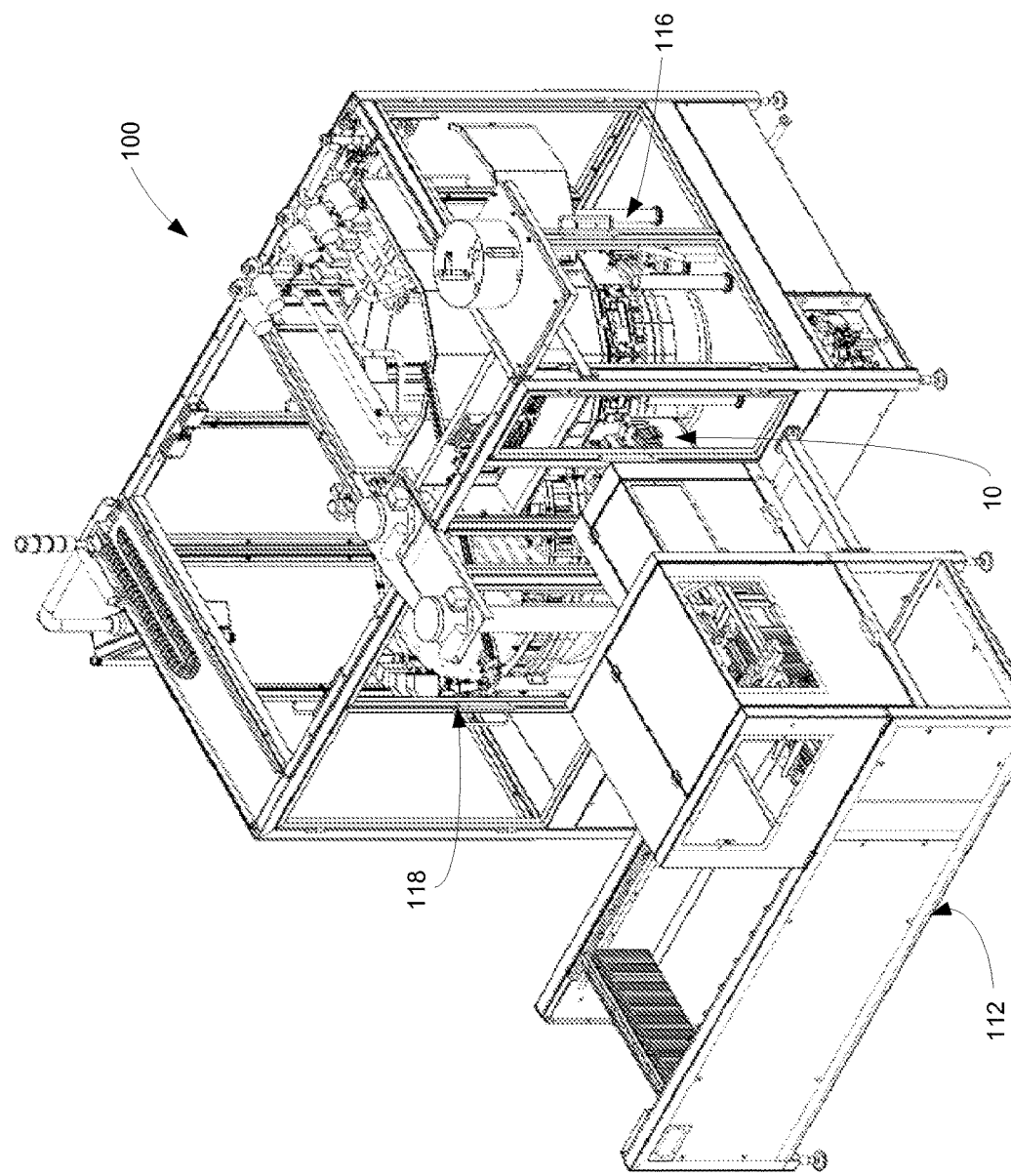
FIG. 4 of the drawings is a perspective view of the aseptic pouch filler having the pouch cleaning assembly of the present disclosure.
Figure 5:
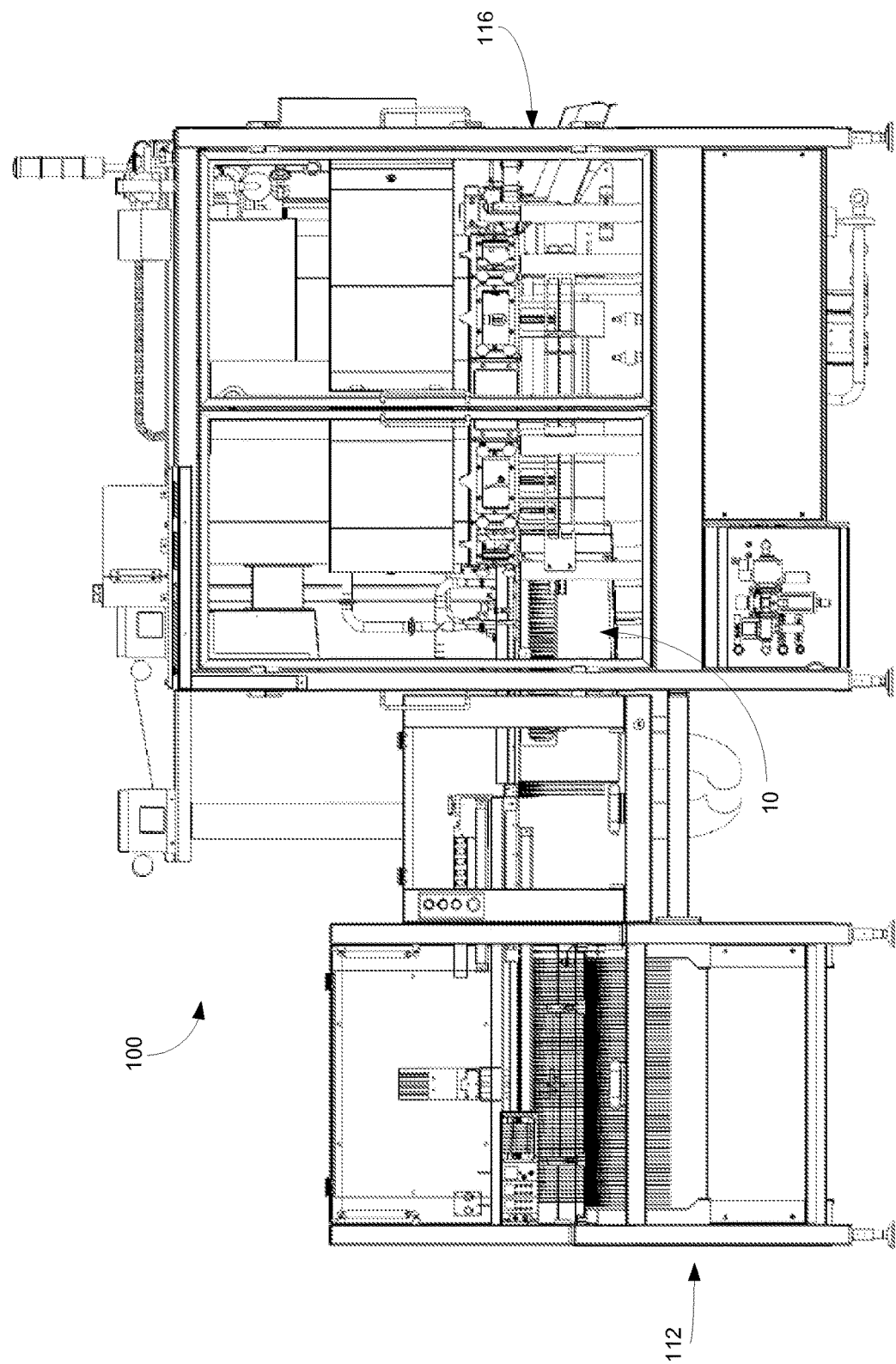
FIG. 5 of the drawings is a side elevational view of an aseptic pouch filler having the pouch cleaning assembly of the present disclosure.
Figure 6:
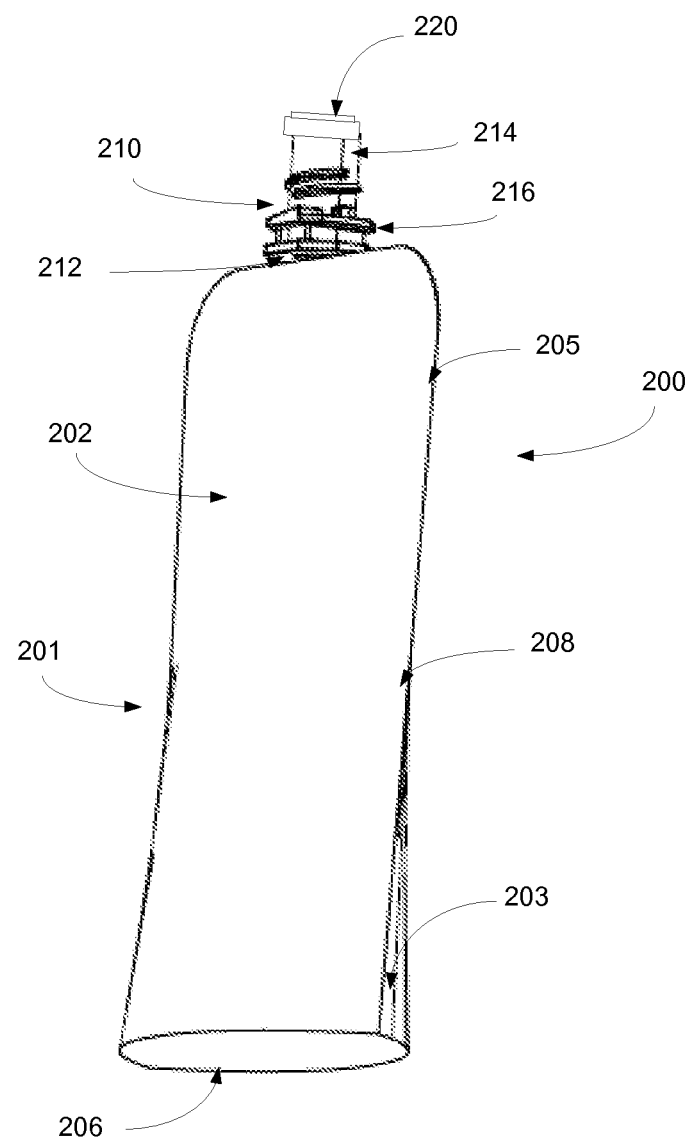
FIG. 6 of the drawings is a perspective view of the pouch assembly of the type that is configured to be directed through the pouch cleaning assembly and structured for use therewith.

Referring now to the drawings and in particular to FIGS. 1 through 3, pouch cleaning assembly 10 for an aseptic filler, such as aseptic filler 100 (FIGS. 4 and 5) is shown. The aseptic filler, for filling an aseptic pouch, includes, in addition to the pouch cleaning assembly 10, cartridge filling assembly 112 upstream thereof and pouch fill assembly 116 and pouch capping assembly 118 downstream thereof. The aseptic pouch, which will be described below with reference to FIG. 6, is directed sequentially through each of the foregoing assemblies so as to be cleaned and filled. The pouch cleaning assembly directs the cleaned pouch into the pouch fill assembly which is maintained within an aseptic zone. It will be understood that an aseptic zone comprises a zone that is under a positive flow of sterilized gas (typically sterilized air), and that has been cleaned to aseptic standards such as those disclosed in Title 21 of the Code of Federal Regulations pertaining to thermally processed low acid foods packaged in hermetically sealed containers overseen by the U.S. FDA, as well as 3-A Sanitary Standards, Inc. and European Hygienic Engineering and Design Group (EHEDG) Standards.

A typical pouch with which the system is associated is shown in FIG. 6 generally at 200. The pouch 200 includes body 201 and spout 210. The body 201 includes first side panel 202, second side panel 203, lower gusset structure 206. The first side panel, the second side panel and the lower gusset structure are coupled together through seals 208 to form cavity 205 configured to retain a flowable material, such as a foodstuff or the like. In many configurations, the gusset structure 206 provides a base surface from which the pouch can be in a standup configuration. Of course, in other configurations, the pouch can be formed from a plurality of panels greater than two panels or from a single panel along with a plurality of folds, wherein the panels cooperate to form the gusset at the lower end thereof. Furthermore, additional structures or gussets (such as side gussets) or gussetless constructions are likewise contemplated). Typically, the cavity is on the order of 60 ml to 500 ml in size. More preferably, the cavity is on the order of 60 ml and 180 ml in size, and more preferably, the cavity is on the order of 90 ml to 120 ml. Of course, variations are contemplated, and the foregoing cavity volumes are exemplary only, and not considered to be limiting. Prior to introduction into the cartridge filling assembly, the pouches have been sterilized through gamma sterilization or the like. As such, the cavities are free of pathogens, and are a sterile environment. The plug has a hermetic seal thereby precluding the passage of material into (or out of) the spout. Generally, such pouches are formed from a multi-layer polymer structure that may include metal or metallized layers, and which may be co-extruded and/or laminated. As will be understood, the pouch (in a capped configuration) is pre-sterilized prior to introduction into filler equipment through, for example, gamma, x-ray, e-beam or other sterilization process, such that the internal cavity of the pouch is free of pathogens and a sterile environment.

Spout 210 is shown as comprising attachment flange 212, outlet tube 214 and grasping flanges 216. The attachment flange is typically sandwiched between the first and second side panels and sealed thereto. The outlet tube 214 provides communication with the cavity 205 and provides the means by which to insert or remove flowable material to and from the cavity. In the configuration shown, the outlet tube 214 is capped with a plug 220 which may extend over the outer surface of the outlet tube 214 or within the confines of the outlet tube to preclude access to the cavity 205. It will be understood that a hermetic seal is formed between the plug and the outlet tube through an interference fit. The grasping flanges 216 extend about the outside of the outlet tube. The grasping flanges provide slots and channels by which the pouch can be grasped, retained, handled, and/or captured by different components of the filling equipment. In the configuration shown, the grasping flanges include outwardly convex side surfaces which, as will be explained below, are advantageous by limiting contact between adjacently positioned abutting pouches within the pouch cleaning assembly. One such configuration of the pouch assembly is shown in co-pending application entitled "Pouch Assembly Having A Plug" and filed as U.S. application Ser. No. 14/860,689, the entire specification of which is hereby incorporated by reference.

Figure 13:
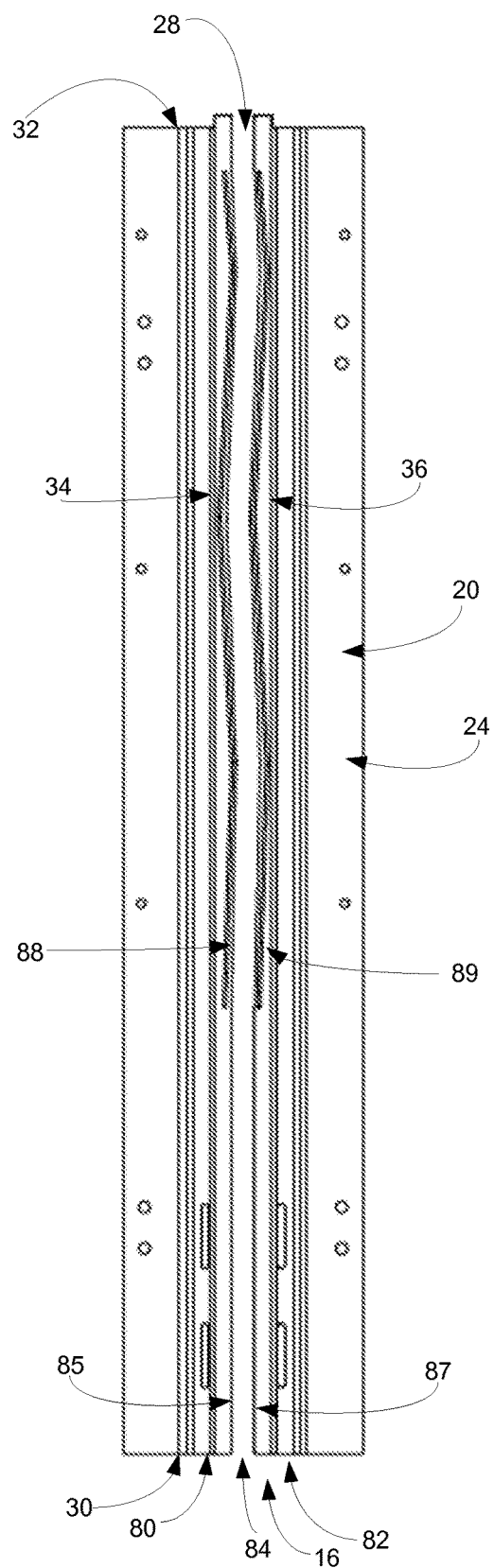
FIG. 13 of the drawings is a top plan view of the base of the treatment chamber along with the guide assembly of the present disclosure.
Figure 14:
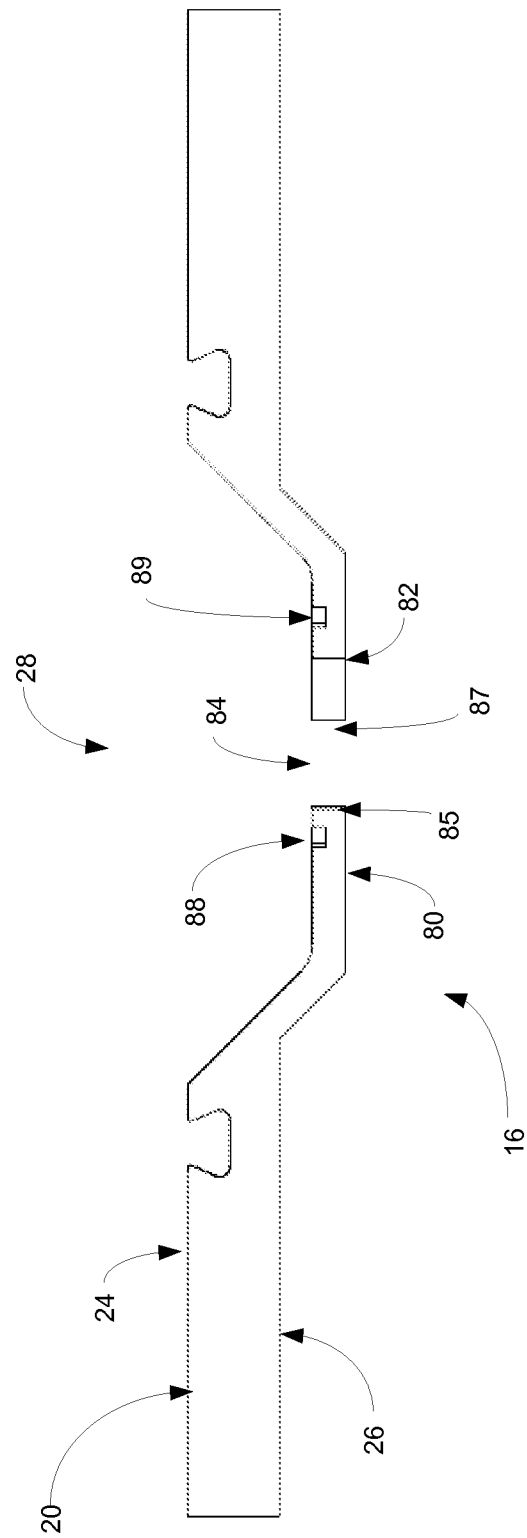
FIG. 14 of the drawings is a front elevational view of the base of the treatment chamber along with the guide assembly of the present disclosure.

Referring again to FIGS. 1 through 3 the pouch cleaning assembly 10 is shown as comprising treatment chamber 12, manifold 14, guide assembly 16 and housing 18. The treatment chamber 12 includes base 20 and surround 22. With reference to FIGS. 13 and 14, the base includes upper surface 24, lower surface 26 and is a substantially elongated planar configuration, wherein the base defines an elongated central channel 28. The channel 28 extends from first end 30 to second end 32, and includes first side 34 and second side 36. In the configuration shown, the first side 34 and second side 36 are substantially parallel to each other so as to define a substantially uniform channel therebetween. It will be understood that the guide assembly is coupled thereto. The base defines the lower end of the treatment zone. It will further be understood that a portion of the spout of the pouch extends above the base with the remainder of the spout and the body being positioned below the base.

Figure 11:
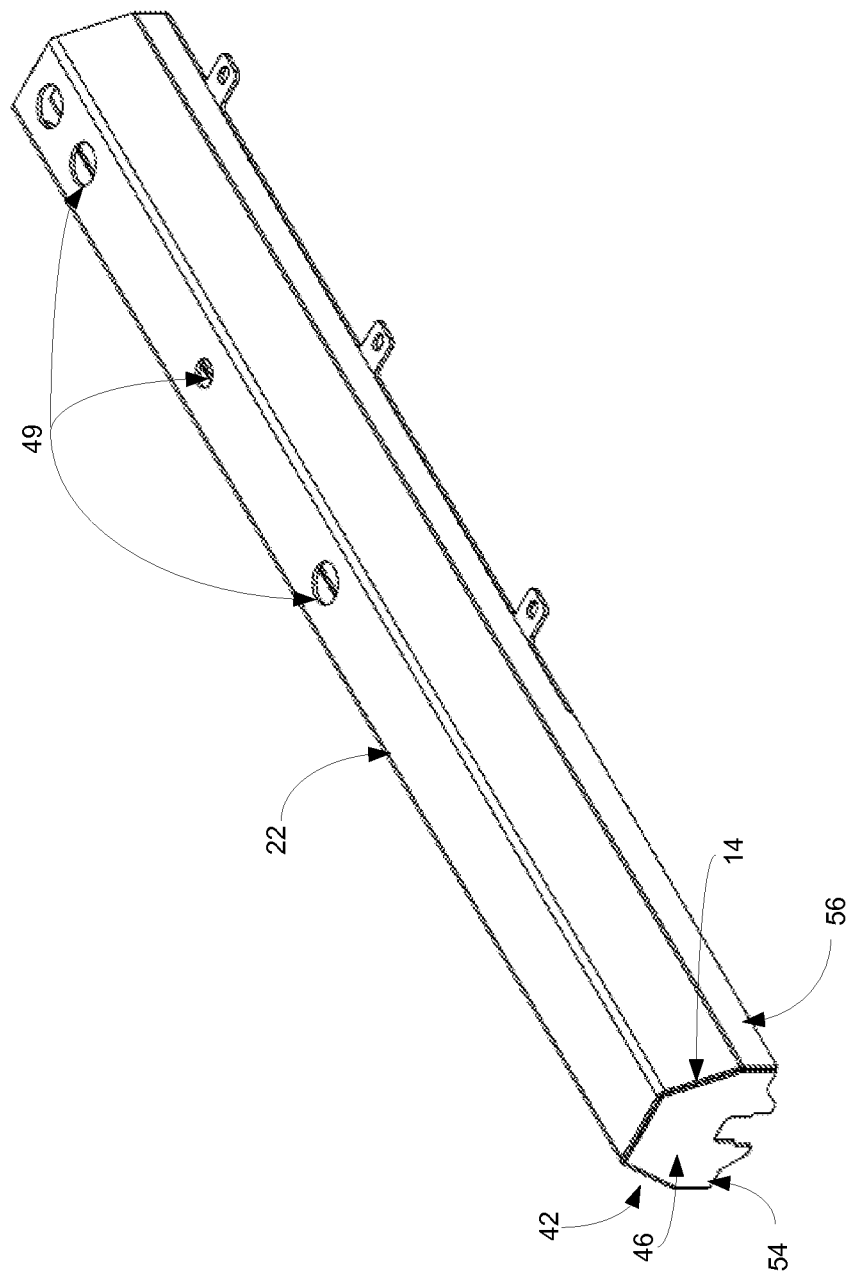
FIG. 11 of the drawings is a perspective view of the surround of the treatment chamber of the pouch cleaning assembly of the present disclosure.

The surround 22 is shown in greater detail in FIG. 11 as comprising upper wall 40, first side wall 42, second side wall 44, first end wall 46 and second end wall 48. With reference to FIG. 2, the surround essentially encapsulates the central channel 28 in a spaced apart orientation. Referring again to FIG. 11, in the configuration shown, the surround is substantially uniform in cross-section, with the upper wall 40 being substantially parallel to the upper surface of the base 20. The first and second side walls depend from the upper wall and extend to the base. In the configuration shown, the side walls include an upper oblique surface, a lower perpendicular surface and a base flange. It will be understood that the surround 22 defines the upper confines of the treatment zone (cooperatively with the base). The second end wall 48 provides closure to the treatment zone at the second end of the surround 22, substantially sealingly engaging the surround 22 and the base 20. Openings, such as opening 49 extend through the surround 22 (and in the case of the opening 49, on the upper wall 40 thereof). A nozzle for injecting cleaning fluid can be positioned so as to extend through the opening 49. In the configuration shown, the opening 49 is positioned proximate the second end of the surround with the direction of the flow to be toward the first end of the surround, and in a direction generally away from the pouch fill assembly 116.

Figure 10:
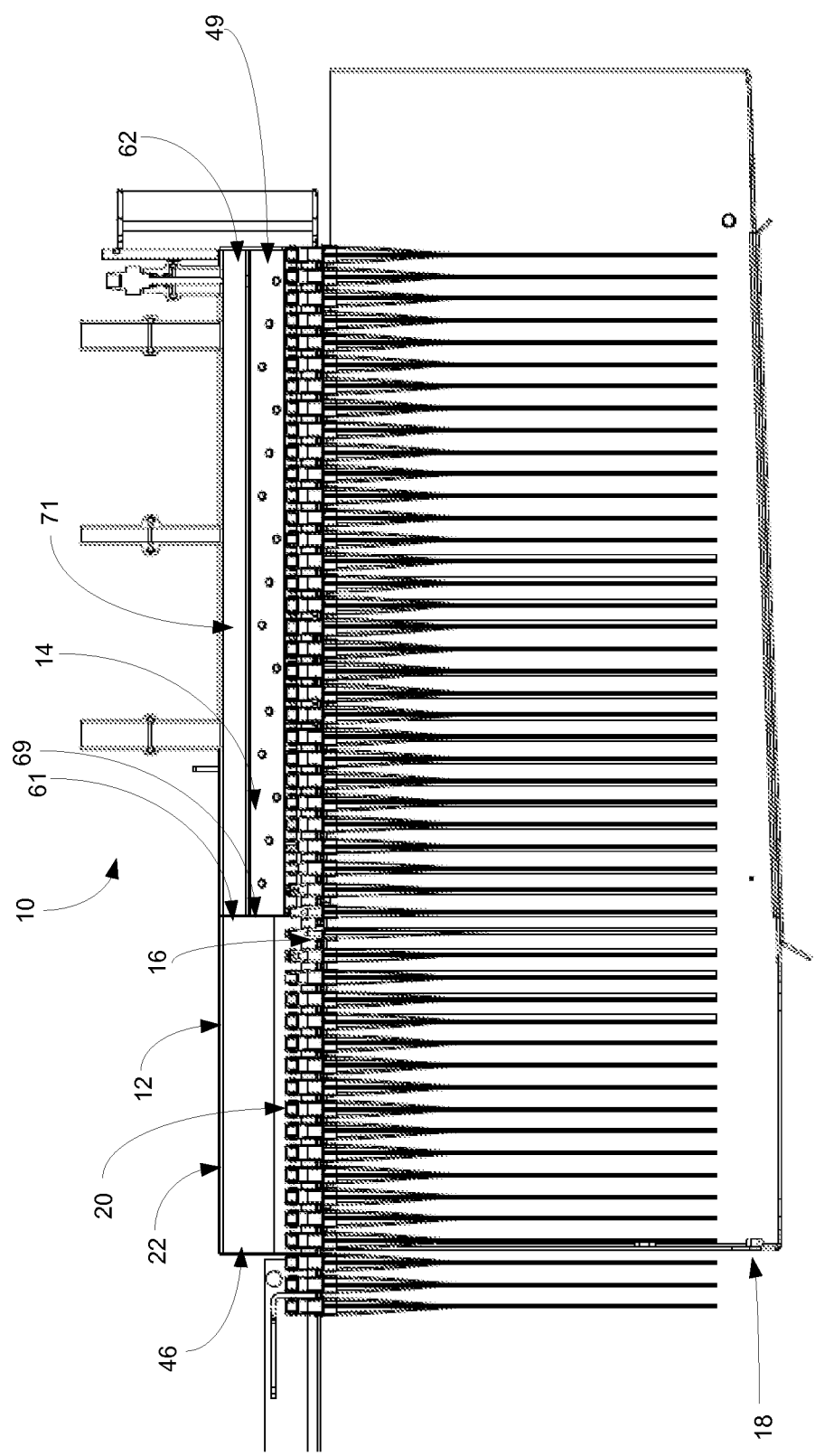
FIG. 10 of the drawings is a cross-sectional view of the pouch cleaning assembly of the present disclosure, taken generally about lines 10-10 of FIG. 1.
Figure 12:
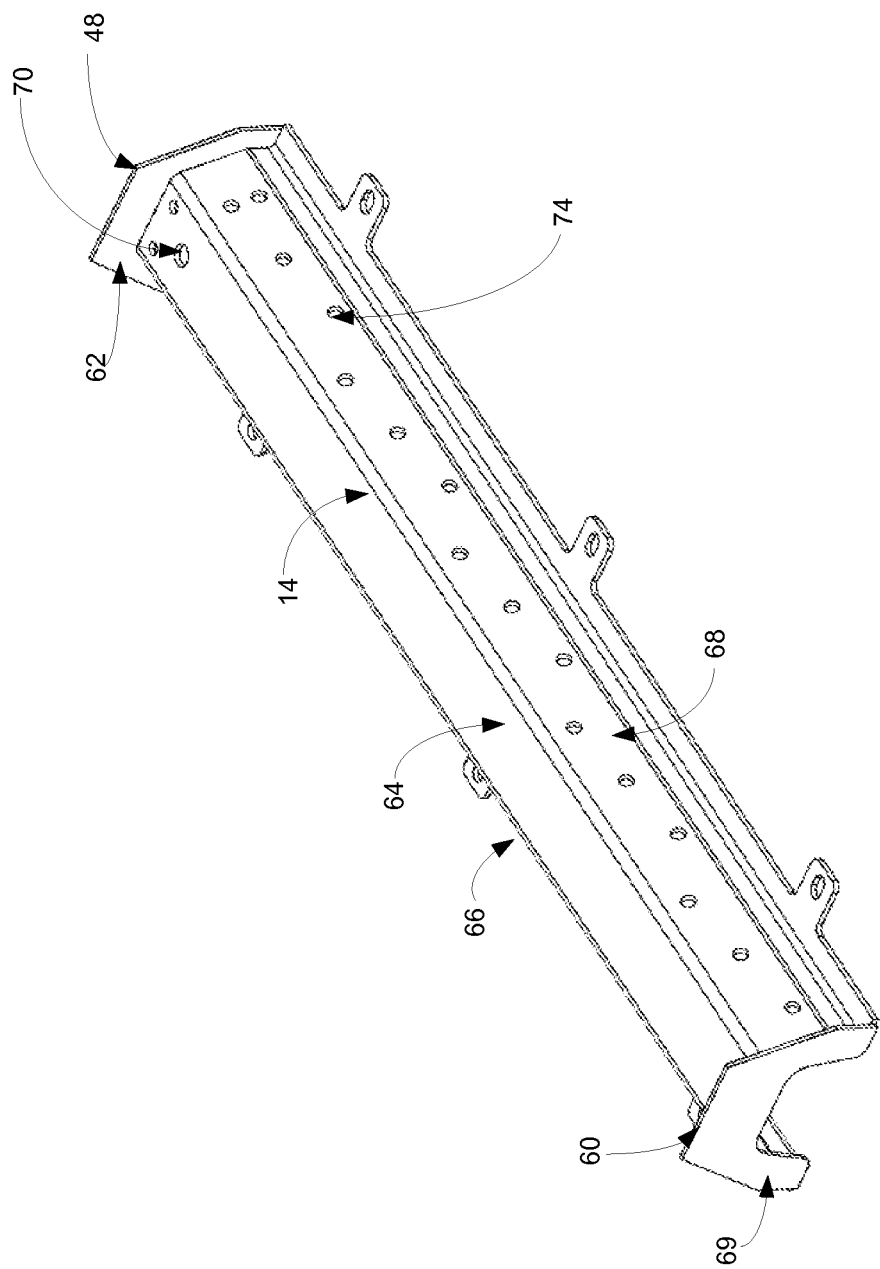
FIG. 12 of the drawings is a perspective view of the manifold of the pouch cleaning assembly of the present disclosure.

With reference to FIG. 2, the manifold 14 is positioned between the base 20 and the surround 22. The manifold 14 generally follows the configuration of the surround 22 while being spaced apart therefrom. With additional reference to FIG. 10, the manifold extends from second end 62 to first end 61, wherein, the second end substantially corresponds to the second end of the surround, and wherein the first end 61 is spaced apart from the first end 46 of the surround 22. With reference to FIG. 12, the manifold 14 includes top wall 64, first side wall 66 and second side wall 68. The top wall 64 substantially corresponds to the upper wall 40 of the surround 22. The first sidewall 66 substantially corresponds to the first sidewall 42 of the surround 22. The second side wall 68 substantially corresponds to the second sidewall 44 of the surround 22 (see FIG. 11). A front wall 69 is positioned between the manifold and the surround proximate the first end 60 thereof. As is shown in FIG. 10, the front wall 69 effectively seals the manifold and the surround 22 proximate the first end thereof, so as to define a manifold cavity 71.

It will be understood that in other configurations, the surround may have a different cross-sectional shape, such as, for example, a circular or semi-circular configuration, a square configuration, a polygonal configuration or the like. It has been found that the shape presented cooperates with the shape of the manifold to cooperatively direct sterilizing cleaning fluid in the desired orientation or the desired direction. It will further be understood that in other configurations, the cross-sectional configuration may be altered along the length thereof. In addition, it is contemplated that the configuration of the surround may be such that the surround side walls taper and meet at the second end, instead of having an end wall at the second end.

The guide assembly 16 is shown in FIGS. 13 and 14 as including first side guide bar 80, second side guide bar 82 defining channel 84 therebetween. The first guide bar 80 includes inner edge 85 and the second guide bar 82 includes inner edge 87. It will be understood that the pouch is suspended by the opposing guide bars at the opposing edges thereof. In such a configuration, at least a portion of the spout extends above the guide bars and into the channel 84. In the configuration shown, the first and second guide bars are substantially planar and, as such, the channel is substantially planar. Preferably, the channel configuration is such that the spouts of adjacent (and often touching) pouches alter position of the contact as they travel along the channel from the first end to the second end, so that the points of contact change, which then effectuates improved cleaning of the surfaces (by exposing previous points of contact). As a result, while the guide bars are substantially planar, the channel is preferably not linear between the first end and the second end. For example, between the first and second end, the channel is defined by a plurality of back and forth line segments that essentially create an undulating channel, while substantially maintaining the width of the channel so as to properly support the grasping spout of the pouch (it will be understood that variations in the channel are permitted, as long as the spouts remain supported and do not irretrievably fall out of the channel). In the configuration shown, the line segments are generally substantially linear and are oblique to each other forming a back and forth pattern. In other configurations, the channel may comprise a curved configuration, such as a sinusoidal pattern or the like. In still other configurations, a combination of linear and curved configurations are contemplated to form the undulations, as well as arbitrary shapes, with the understanding that such a configuration of the channel (that is back and forth undulation) will alter the point of contact between adjacent pouches positioned therealong. In the configuration shown, the guide bars may be separate components that are coupled to the base, whereas, in other configurations, the guide assembly may be integrally formed with the base or the surround of the treatment chamber.

Additionally, elongated grooves 88, 89 are positioned along the side of each of the inner edges 85 and 87 and extend at least partially between the first and second ends of the guide assembly. The elongated grooves extend into the surface of the first and second guide bars, and are spaced apart from the inner edges so that when a spout is positioned within the channel 84, a portion of the grasping flange (in the configuration shown, the upper grasping flange) extends over the elongated grooves. As such, when the cleaning fluid is directed through the chamber, some of the cleaning fluid is directed into the elongated grooves and toward the lower surface of the grasping flange, to, in turn, clean the lower side of the grasping flange. The combination of the undulations of the channel, and the position of the elongated grooves, the underside of the grasping flange is likewise exposed to cleaning fluid, and in turn, cleaned. It will be understood that the underside surface is placed within the aseptic zone, and, as such, is to be sterilized.

Figure 15:
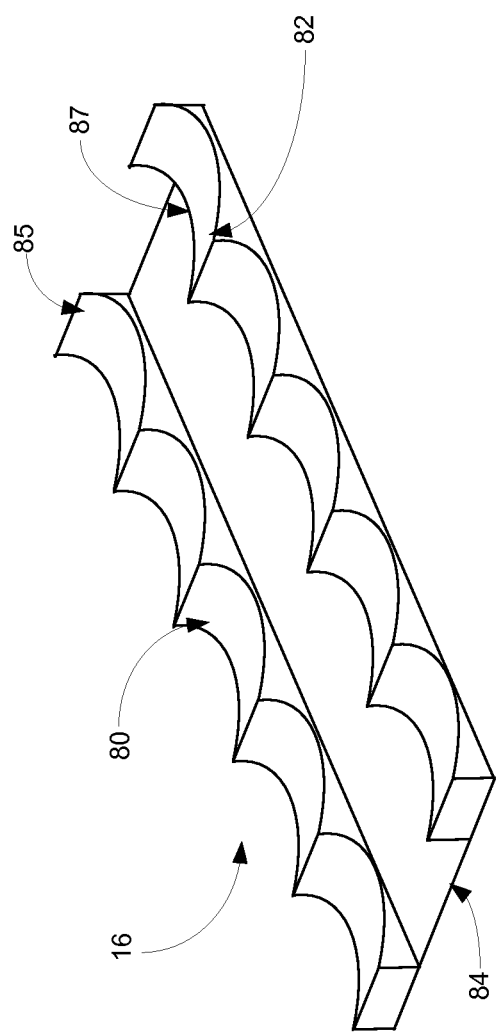
FIG. 15 of the drawings is a second embodiment of the guide assembly of the present disclosure, showing, essentially vertical undulations which vertically provide relative movement between adjacent pouches.

In another configuration, shown in FIG. 15, the channel comprises opposing guide bars that include undulations in the form of vertical surface alterations. In the configuration shown, the opposing guide bars include a vertically undulating (or curved surface). Such a surface allows for vertical (up and down) motion of the pouches, and relative motion between the pouches. Such a configuration further allows for the cleaning fluid to be directed between the pouch and the undulations and additionally at the lower surface of the upper one of the grasping flanges. As such, cleaning fluid reaches the required areas, and, at the same time, the relative movement of adjacent pouches allows for the variation of the contact point for the adjacent pouches, and allows for cleaning fluid to be directed below the upper surface of the upper one of the grasping flanges. It is further contemplated that such undulations may include both vertical and horizontal component wherein the spouts of the pouches will have relative movement in multiple dimensions relative to adjacent pouches, which may include inclined movement, left and right as well as up and down movement and/or a twisting movement. With such an undulation, the relative points of contact between adjacent spouts (or other components positioned within the treatment chamber) are altered along the channel so as to expose the same to the cleaning preparation. In other words, the channel is undulating in at least one of a vertical and a horizontal direction (i.e., the undulation may have horizontal and vertical components of movement) along the length thereof sufficient so as to substantially expose the relative points of contact between adjacent ones of the plurality of spouts so as to expose the same to the cleaning preparation.

Figure 7:
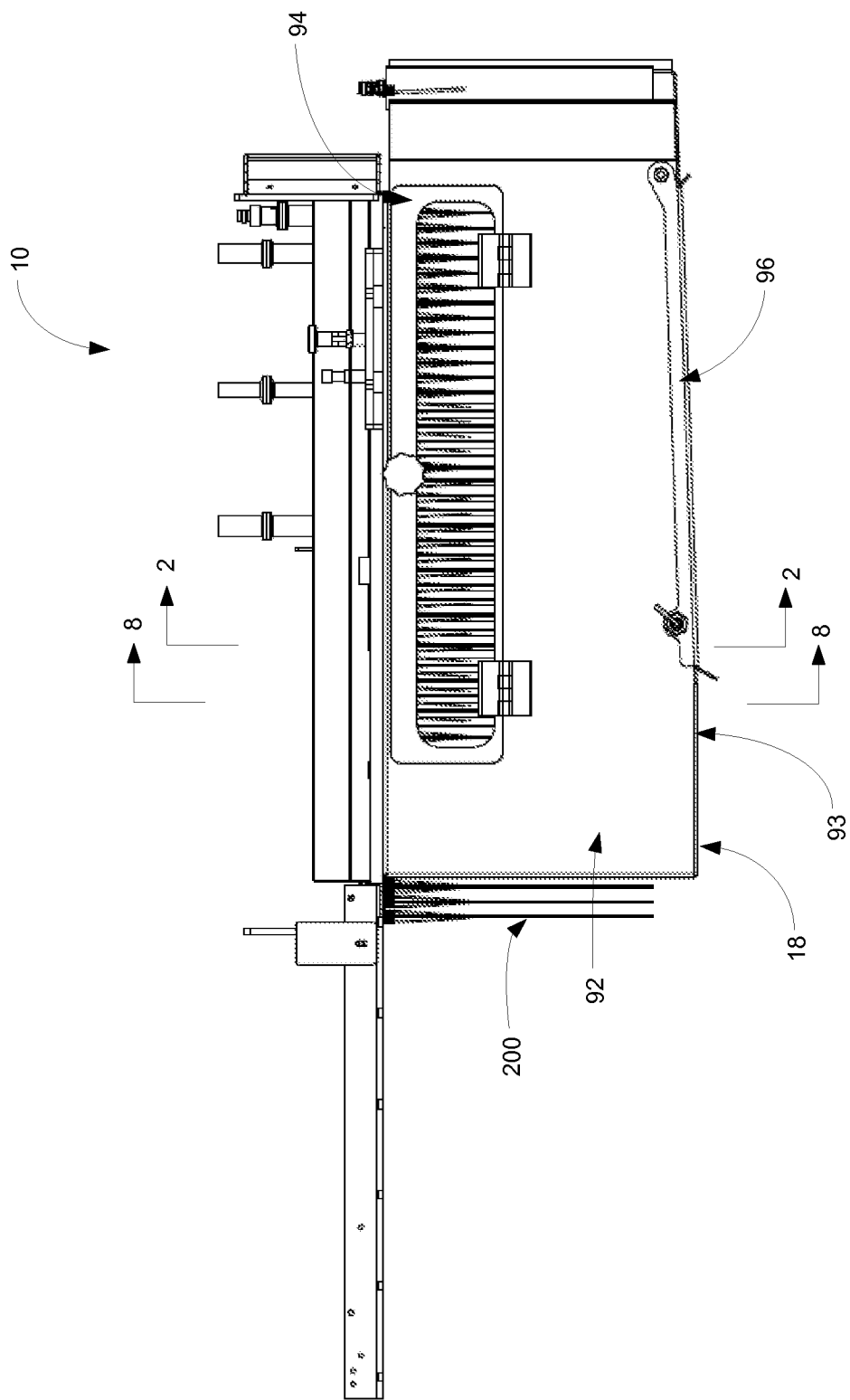
FIG. 7 of the drawings is a side elevational view of the pouch cleaning assembly of the present disclosure.
Figure 8:
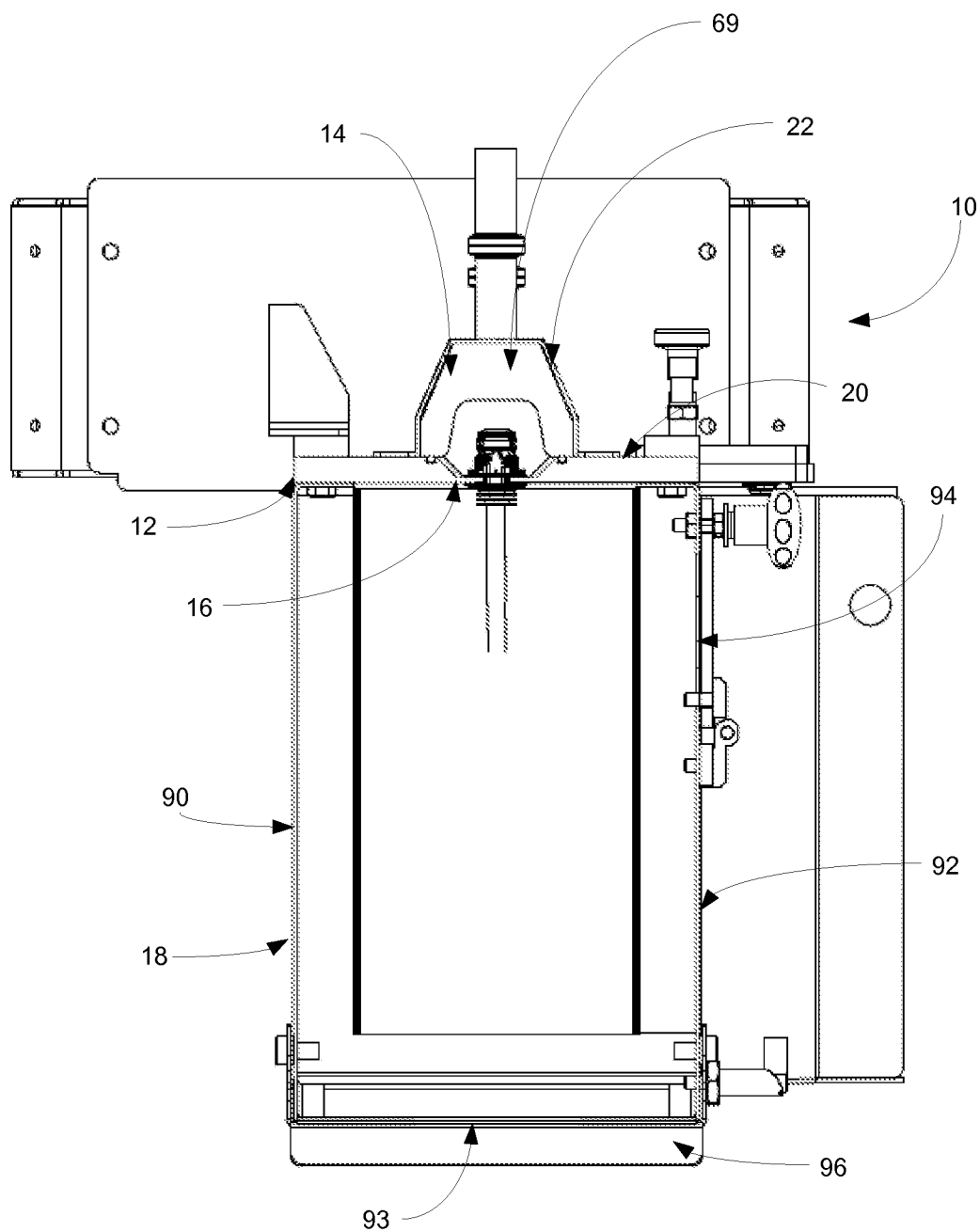
FIG. 8 of the drawings is a cross-sectional view of the pouch cleaning assembly of the present disclosure, taken generally about lines 8-8 of FIG. 7.
Figure 9:
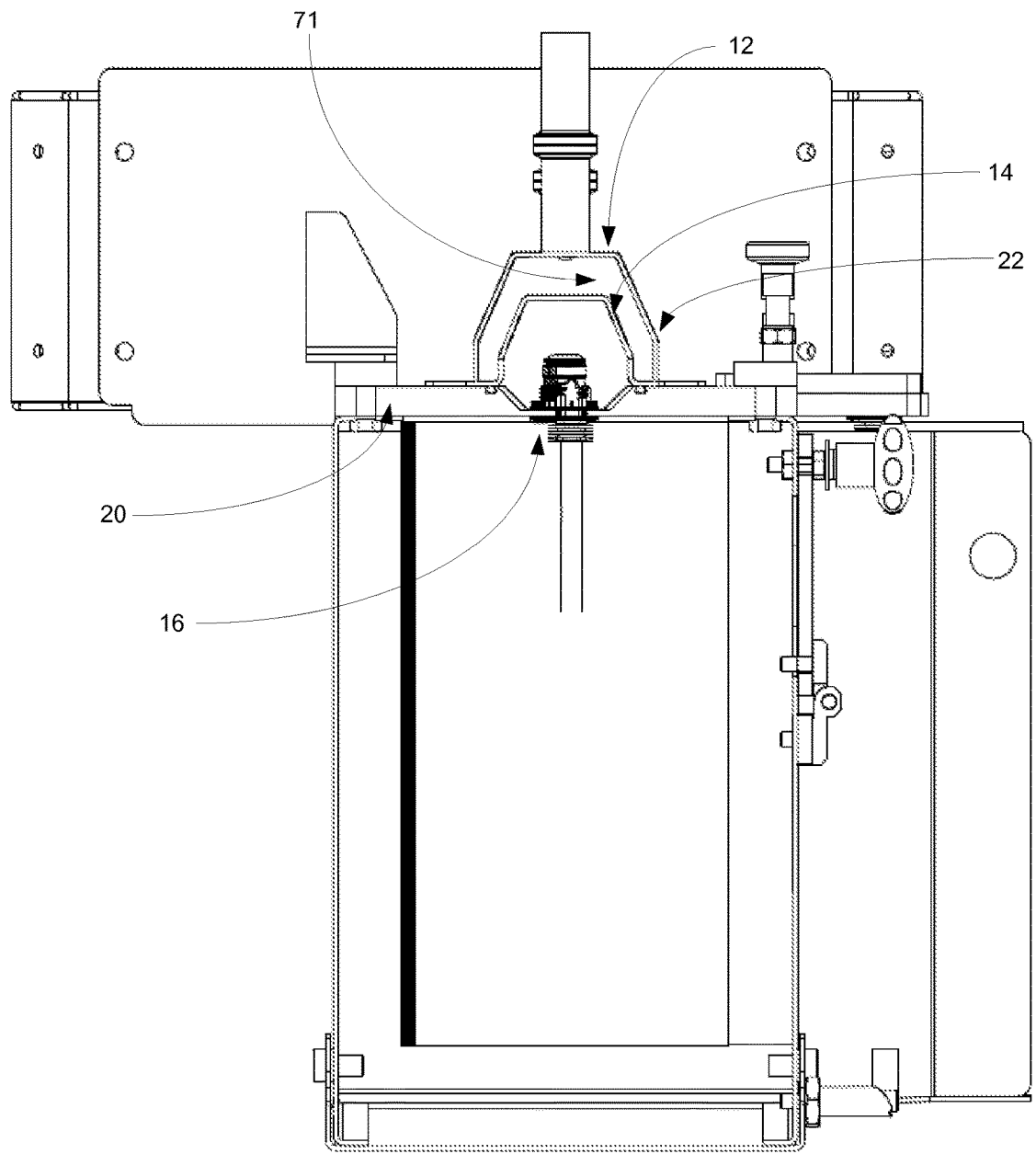
FIG. 9 of the drawings is a cross-sectional view of the pouch cleaning assembly of the present disclosure, taken generally about lines 2-2 of FIG. 7.

With reference to FIGS. 3, 7 and 8, housing 18 may extend below the base 20 and may envelope the remainder of the pouch that does not extend into and above the central channel 28 of the base 20 of the treatment chamber 12. The housing 18 includes side walls 90, 92 and base wall 93. The side walls 90, 92 are positioned on opposite sides of each other and are substantially parallel to each other. That is, the side wall 90 extends from the lower surface of the base on one side thereof and extends between the first and second ends thereof. The side wall 92 extends from the lower surface on the opposite side thereof from the side wall 90 and extends between the first and second ends thereof. An access opening, such as side door 94 may be provided for both visual inspection of the inside of the cavity formed thereby, and for access thereto. In the configuration shown, the side door is hingedly mounted to the side wall and covers an opening formed in the side wall. A closure member in the form of a threaded knob facilitates selective closing and opening of the side door 94. While the side door 94 is shown as being transparent, other configurations are contemplated. It is also contemplated that multiple openings may be presented.

The base wall 93 extends across between the side walls 90, 92 so as to enclose the bottom end of the cavity. The base wall is generally parallel to the base 20 of the treatment chamber 12 and spaced apart therefrom. The side walls 90, 92 are generally parallel to each other as well and spaced apart from each other. Together, the base 20, the side walls 90, 92 and the base wall 93 define the cavity for the remainder of the pouch that is not extended into the treatment chamber. The cross-sectional configuration of the cavity substantially matches the configuration of the pouch such that the pouch can travel therethrough without generally impinging on the side walls or on the bottom wall, even as the pouch transitions back and forth. A door 96 may be positioned across the base wall 93 to provide ingress into the cavity from below, or for purposes of drainage. Additionally, an exhaust opening 95 may be presented in the bottom surface which is coupled to a suction device, for example, so as to direct air or other gasses, or liquids out of the cavity and to further draw the cleaning preparation into the treatment chamber, and, to, in turn, direct the flow of the cleaning preparation from the second end toward the first end of the treatment chamber.

In operation, the pouches are provided sequentially to the pouch cleaning assembly. It will be understood that the manner in which the pouches are sequentially provided can be varied without departing from the scope of the disclosure. As the pouches are provided, they are directed to the first end of the treatment chamber. In particular, the pouches matingly engage with the guide assembly 16 so as to be captured thereby and so as to be slidably positionable therealong. In the configuration shown, the spout includes grasping flanges 216 (FIG. 6) that interface with the guide assembly, and in particular, the inner edges of the first and second guide bars. Initially, the pouch is positioned proximate the first end of the guide assembly (and, in turn, the central channel 28).

With reference to FIGS. 1 through 3 and 7 through 9, with a portion of the spout of the pouch extending into the treatment chamber, the remainder of the pouch (that is, the body thereof) extends into the cavity formed by the side walls 90, 92, the base wall 93 and the lower surface 26 of the base 20. Generally, the configuration is such that the pouch is generally perpendicular to each of the walls.

As successive pouches are introduced, the pouches abut each other so as to move along through the treatment chamber. It will be understood that in the configuration shown, it is desirable that the pouches contact adjoining pouches about the grasping flange or other structure, wherein the contact can be minimized. In the configuration shown, contact is preferably maintained along a point that is where the curved configurations of the adjacent grasping flanges meet.

Figure 16:
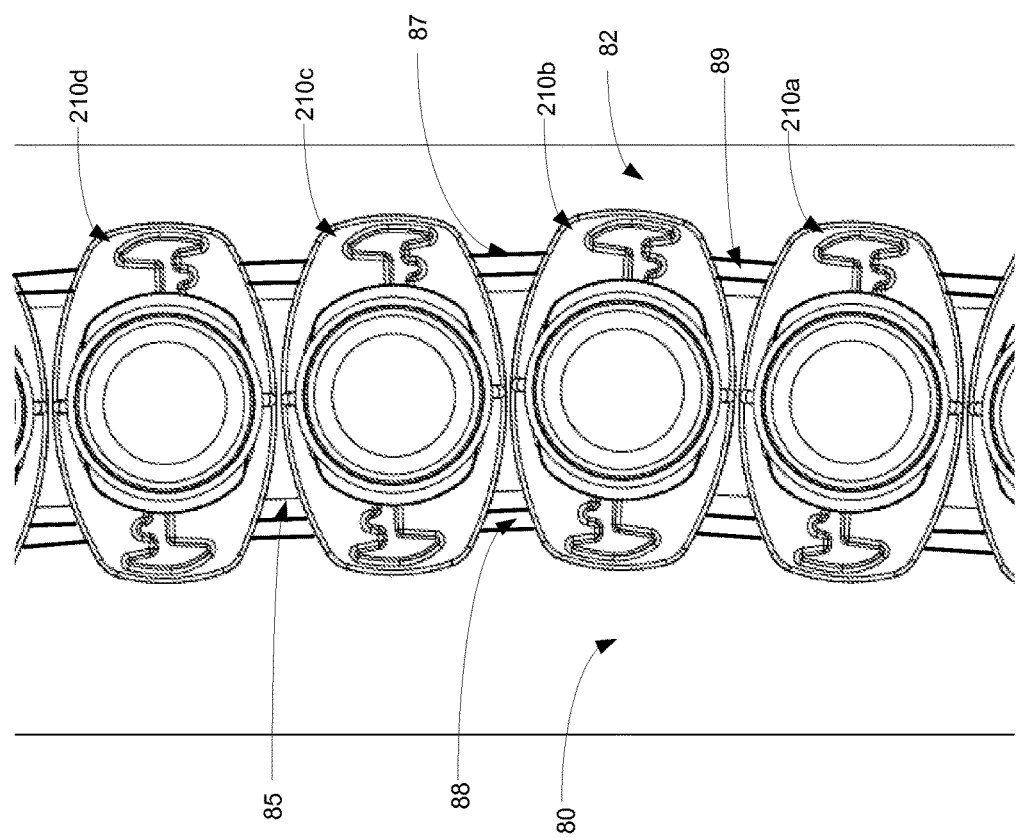
FIG. 16 of the drawings is a top plan view of adjacent pouches within the guide assembly, showing, in particular, the relative position of adjacent pouches as the pouches progress through the undulations defined in the channel of the guide assembly.

As each pouch moves along the channel 84 defined by the guide assembly, the pouches undulate toward and away from the opposing sides of the base (that is, toward and away from opposing side walls). As the pouches move along the channel, the point of contact between the adjacent pouches changes as the pouches are moving relative to each other in a side to side manner as they extend along the length thereof. As such, a previous point of contact between adjacent pouches becomes exposed, and a previously exposed portion becomes the point of contact between pouches. For example, as is shown in FIG. 16, the spouts 210a, 210b, 210c and 210d are proximate a region where the channel changes direction (in this case from a direction toward the second guide bar to a direction toward the first guide bar). In such a configuration, the spouts of pouches 210a and 210b abut generally centrally along the outer convex shape of the grasping flanges. Similarly, the spouts of the pouches 210c and 210d abut generally centrally along the outer convex shape of the grasping flanges. On the contrary, the spouts of the pouches 210b and 210c abut in an offset fashion, that is, slightly off center. That is, the central portion of the spout 210c is contacting to the left of the central portion of the spout 210b. Thus, at the very least, the central portion of the spout 210b is fully exposed and can be cleaned by the cleaning preparation.

Figure 17:
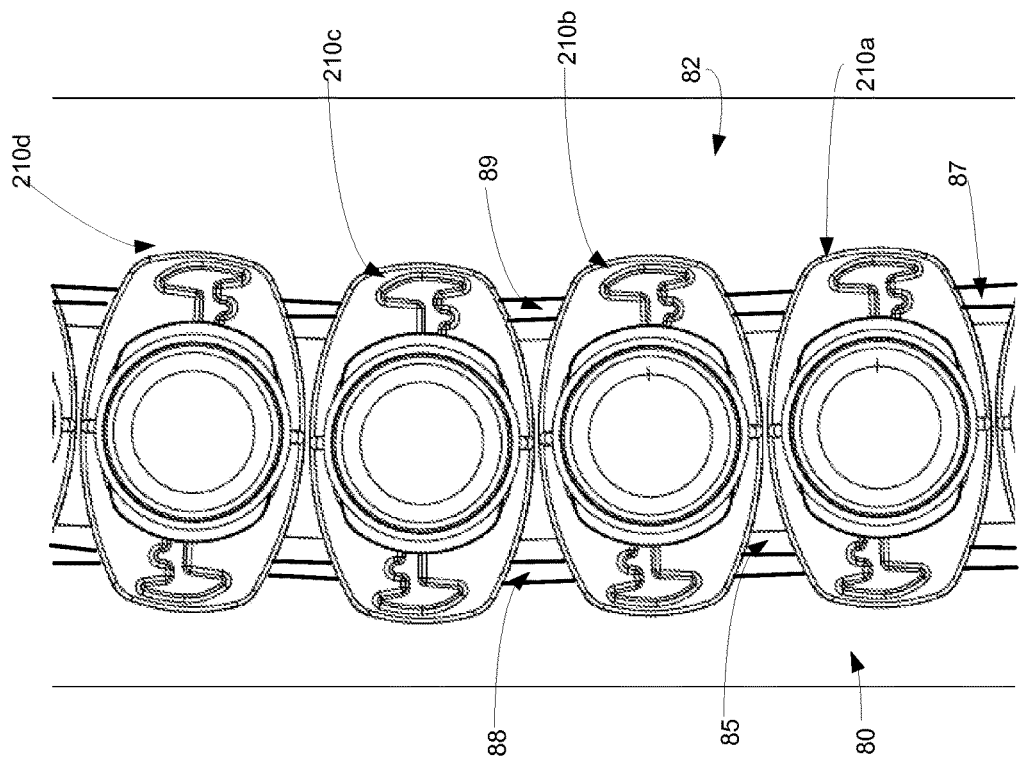
FIG. 17 of the drawings is a top plan view of adjacent pouches within the guide assembly, showing, in particular, the relative position of adjacent pouches as the pouches progress through the undulations defined in the channel of the guide assembly.

Focusing now on FIG. 17, the same spouts are reaching another region wherein the pouches are directed back toward the second guide bar after being directed toward the first guide bar. In such an orientation, the spouts 210a and 210b abut generally about the center of the outer convex shape of the grasping flanges. The spouts 210c and 210d abut in a slightly offset fashion, the central region of the spout 210c is to the right of the central region of the spout 210d. The spout 210b and spout 210c abut in an offset fashion; the central region of the spout 210b abuts to the right of the central region of the spout 210c. Between the movements of the spouts 210a through 210d, each portion of the spout (and the grasping flanges that form the abutting configuration) are exposed to the cleaning preparation. Of course, further undulations, or undulations in different shapes and orientation (that is, up and down, left and right, or both) can achieve the exposure of the surfaces of the spout that are within the treatment chamber 12.

The process of insertion can continue sequentially pouch after pouch being introduced into the first end of the treatment chamber. Eventually, the pouches reach the second end of the treatment chamber. Along the chamber, the pouches undulate from side to side along the channel toward the second end. As the pouches exit the second end, they are directed into a filler, for example, such as aseptic filler 100 of FIG. 4, which is disclosed in co-pending application entitled "Rotary Filling Device For Aseptic Filling of Pouches" and filed as U.S. application Ser. No. 14/860,686, the entire specification of which is hereby incorporated by reference.

At the same time that the pouches are directed along the guide assembly 18 from the first end to the second end of the treatment chamber 12, the portion of the pouches that are positioned within the treatment chamber 12 are exposed to chemical treatment, through, for example, a cleaning preparation (in the form of a vapor, a liquid, a gas or a combination thereof). In the configuration shown, it is contemplated that a hydrogen peroxide vapor is transmitted through the treatment chamber at an elevated temperature in a directed manner to clean the surfaces of the pouch. In other configurations, different fluids and mechanisms may be utilized in order to effectuate cleaning. That is, gasses, or othercombinations of gasses, vapors, liquids and the like can be utilized.

In particular, the different cleaning preparations are directed through the openings 49 of the surround 22. The cleaning solutions enter the manifold cavity 71 and are bounded by the second end wall 48, the front wall 69 and the manifold and surround. Continued insertion of cleaning solutions, combined with the relative pressure difference between the manifold cavity 71 and the cavity within the surround outside of the manifold cavity direct the cleaning preparation through the openings 72, 74 and toward and into contact with the pouches that are positioned within the central channel 28. The cleaning preparation, preferably, again due to the relative pressures and flow properties, is directed generally away from the second end of the surround and toward the first end of the surround, and eventually through the outlet 95 (FIG. 3). Within the treatment chamber, the cleaning preparation is in a positive flow so as to be directed therein and therethrough. Due to the variations in the position of the pouches, and the time that the pouches are present within the treatment chamber, the cleaning preparation effectively contacts the entirety of the spout portion that is maintained within the treatment zone. In addition, as the relative position of adjacent pouches is varied, the contact region between adjacent pouches is likewise cleaned. Additionally, some of the cleaning preparations are directed into the elongated grooves 88, 89 so as to be exposed to the lower surface of the grasping flanges.

Eventually, the pouches exit from the second end of the treatment chamber 12, the pouch is directed into the filling equipment. The pouches have been sanitized so as to be sterile and are prepared for direction into an aseptic filler, for example, of the type disclosed in the above identified co-pending application.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A pouch cleaning assembly comprising:
    a treatment chamber including an elongated central channel extending therethrough;
    a guide assembly having a first side guide bar and a second side guide bar, the guide bars defining a channel therebetween, structurally configured to facilitate the retention of spouts of a plurality of pouches in slidable engagement along the first and second guide bar, wherein any abutment of adjacent portions of the plurality of pouches within the treatment chamber define relative points of contact, the channel positioned within the elongated central channel, wherein the channel is undulating in at least one of a vertical and a horizontal direction along the length thereof sufficient so as to substantially expose the relative points of contact between adjacent ones of the plurality of spouts so as to expose the same to the cleaning preparation.

2. The pouch cleaning assembly of claim 1 wherein the channel is undulating in a back and forth manner, with the channel being substantially planar.

3. The pouch cleaning assembly of claim 2 wherein the channel is defined by a plurality of linear segments that are obliquely positioned relative to each other, with the linear segments being substantially planar.

4. The pouch cleaning assembly of claim 3 wherein the channel includes a substantially uniform width between a first end and a second end thereof.

5. The pouch cleaning assembly of claim 2 further comprising a first elongated groove extending along a first side of the channel, and a second elongated groove extending along a second side of the channel, the first and second elongated grooves positioned so that a portion of a spout overlies the first and second elongated grooves as a spout travels along the channel.

6. The pouch cleaning assembly of claim 1 wherein the channel is undulating in an up and down manner.

7. The pouch cleaning assembly of claim 1 wherein the treatment chamber further comprises:
a base having the central channel defined therein, the base having an upper surface;
a surround having an upper wall and opposing depending sidewalls, the upper wall being spaced apart from the upper surface, with the opposing depending sidewalls extending between the upper wall and the upper surface of the base, the base and the surround defining a cavity, the cavity having a first end and a second end.

8. The pouch cleaning assembly of claim 7 wherein the surround further includes at least one opening configured to direct a cleaning preparation into the cavity defined by the base and the surround.

9. The pouch cleaning assembly of claim 8 wherein the at least one opening comprises a plurality of openings, wherein the plurality of openings are defined in the upper wall.

10. The pouch cleaning assembly of claim 7 wherein the first end and the second end of the surround further include a wall extending between the surround and the base, and wherein the surround has a substantially uniform cross-sectional configuration.

11. The pouch cleaning assembly of claim 8 further including a manifold positioned between the surround and the central channel, to, in turn, define a manifold cavity between the manifold and the surround, the manifold having a plurality of openings providing fluid communication between the manifold cavity and the central channel.

12. The pouch cleaning assembly of claim 11 wherein the manifold further includes a top wall with a first sidewall and a second sidewall depending from the top wall on opposing sides of the central channel, and extending to the upper surface of the base, the plurality of openings being positioned in each of the first sidewall and the second sidewall.

13. The pouch cleaning assembly of claim 12 wherein the manifold includes a first end that is spaced apart from the first end of the central channel, and a second end that substantially corresponds to the second end of the central channel.

14. The pouch cleaning assembly of claim 13 wherein the manifold further includes a front wall sealingly coupling the first end of the manifold and the surround.

15. The pouch cleaning assembly of claim 11 wherein the treatment chamber is in positive flow.

16. The pouch cleaning assembly of claim 15 wherein the opening of the surround is positioned proximate the second end of the central channel, with an outlet from the treatment chamber being positioned proximate the first end of the central channel, so that the positive flow is directed primarily from the second end toward the first end.

17. The pouch cleaning assembly of claim 1 wherein the treatment chamber is in positive flow, with an outlet from the treatment chamber being positioned proximate the first end of the central channel, so that the positive flow is directed primarily toward the first end of the central channel.

18. The pouch cleaning assembly of claim 1 further comprising a housing positioned below the treatment chamber, the housing structurally configured to retain a portion of the pouch outside of the treatment chamber while a portion of the pouch extends through the central channel and into the treatment chamber.

* * * * *